United States Patent

Zou et al.

[11] Patent Number: 5,902,604
[45] Date of Patent: May 11, 1999

[54] SUBMICRON LIPOSOME SUSPENSIONS OBTAINED FROM PRELIPOSOME LYOPHILIZATES

[75] Inventors: Yiyu Zou; Waldemar Priebe; Roman Perez-Soler, all of Houston, Tex.

[73] Assignee: Board of Regents, The University of Texas System, Austin, Tex.

[21] Appl. No.: 08/468,791

[22] Filed: Jun. 6, 1995

[51] Int. Cl.⁶ ................................................. A61K 9/66
[52] U.S. Cl. ..................... 424/450; 264/4.1; 428/402.2
[58] Field of Search ..................... 424/450; 264/4.1; 428/402.2

[56] References Cited

U.S. PATENT DOCUMENTS

| | | | |
|---|---|---|---|
| 4,201,773 | 5/1980 | Horton et al. | 424/180 |
| 4,311,712 | 1/1982 | Evans et al. | 424/365 |
| 4,522,803 | 6/1985 | Lenk et al. | 424/1.1 |
| 4,537,882 | 8/1985 | Horton et al. | 514/34 |
| 4,558,579 | 12/1985 | Fountain et al. | 72/56 |
| 4,812,312 | 3/1989 | Lopez-Berestein | 424/417 |
| 4,855,089 | 8/1989 | Wallach | 264/4.1 |
| 4,863,739 | 9/1989 | Perez-Soler et al. | 424/450 |
| 4,911,928 | 3/1990 | Wallach | 424/450 |
| 4,950,432 | 8/1990 | Mehta et al. | 264/4.6 |
| 4,975,282 | 12/1990 | Cullis et al. | 424/450 |
| 4,999,199 | 3/1991 | Anaissie et al. | 424/450 |
| 5,032,404 | 7/1991 | Lopez-Berestein | 424/450 |
| 5,132,290 | 7/1992 | Priebe et al. | 514/34 |
| 5,178,875 | 1/1993 | Lenk et al. | 424/450 |

FOREIGN PATENT DOCUMENTS

| | | |
|---|---|---|
| 0 140 085 A2 | 5/1985 | European Pat. Off. . |
| 0 193 414 A2 | 9/1986 | European Pat. Off. . |
| 0 220 797 A2 | 5/1987 | European Pat. Off. . |
| 0282405 | 9/1988 | European Pat. Off. . |
| 0613685 | 9/1994 | European Pat. Off. . |
| 2700954 | 8/1994 | France . |
| 60-155109 | 8/1985 | Japan . |
| 6183953 | 7/1994 | Japan . |
| 6227966 | 8/1994 | Japan . |

| | | |
|---|---|---|
| WO86/00238 | 1/1986 | WIPO . |
| 87/00043 | 1/1987 | WIPO . |
| WO89/11850 | 12/1989 | WIPO . |
| WO 92/11842 | 7/1992 | WIPO . |

OTHER PUBLICATIONS

Japanese Abstract, JP 62–93615 A (Nippon Oils & Fats Co. Ltd.), Oct. 21, 1994.

(List continued on next page.)

*Primary Examiner*—Jyothsna Venkat
*Attorney, Agent, or Firm*—Arnold White & Durkee

[57] ABSTRACT

This invention provides an aqueous/t-butanol solvent-system, facile reconstitute, submicron-reconsitiute preliposome-lyophilaye and method of its preparation and use.

In one embodiment this entails a modified method for the preparation of a submicron and stable liposome formulation of the non-cross-resistant anthracycline Annamycin is described. The optimal lipid composition was DMPC:D-MPG at a 7:3 molar ratio and the optimal lipid:drug weight ratio 50:1. The selected formulation is a preliposome lyophilized powder that contains the phospholipids, Annamycin, and 1.7 mg Tween 20 per mg of Annamycin. The liposome suspension is obtained on the day of use by adding normal saline at 37° C. (1 ml per mg Annamycin) and hand-shaking for one minute. The presence of Tween 20 is essential in shortening the reconstitution step (from >2 hours to 1 minute), avoiding the early formation of free drug crystals, and reducing the median particle size (from 1.5 $\mu$m to 0.15–0.20 $\mu$m) without destruction of the liposome vesicles. The chemical stability of the preliposome powder at room temperature was >3 months and the chemical and physical stability of the liposome suspension at room temperature >24 hours. The in vitro cytotoxicity of the formulation was equivalent to that prepared by the standard evaporation method. The results of the study indicate that small amounts of surfactant may be used to enhance the reconstitution step and reduce the liposome size of lyophilized liposome formulations of lipophilic drugs.

2 Claims, 6 Drawing Sheets

OTHER PUBLICATIONS

Perez–Soler et al, "Anthracycline Antibiotics with High Liposome Entrapment: Structural Features and Biological Activity," Cancer Research 50: 4260–4266 (Jul. 15, 1990).

Zou et al, "Antitumor Activity of Free and Liposome–entrapped Annamycin, A Lipophilic Anthracycline Antibiotic with Non–Cross–Resistance Properties," Cancer Research 54:1479–1484 (Mar. 15, 1994).

McCutcheon's "Emulsifiers & Detergents," vol. 1, p. 201, North American Edition (1993).

Kronberg et al, "Preparation and Evaluation of Sterically Stabilized Liposomes: Colloidal Stability, Serum Stability, Macrophage Uptake, and Toxicity," J. Pharm. Sci. 79(8):667–671 (1990).

Singer et al, "Time– and Dose–dependent Changes in Ejection Fraction Determined by Radionuclide Angiography After Anthracycline Therapy," Cancer Treatm. Rep., 62(6):945–948 (1978).

Herman et al, "Prevention of Chronic Doxorubicin Cardiotoxicity in Beagles by Liposomal Encapsulation," Cancer Res. 43:5427–5432 (1983).

Rahman et al, "A Phase I Clincical Trial and Pharmacokinetic Evaluation of Liposome–Encapsulated Doxorubicin," J. Clin. Oncol. 8:1093–1100 (1990).

Gabizon et al, "Prolonged Circulation Time and Enhanced Accumulation in Malignant Exudates of Doxorubicin Encapsulated in Polyethylene–glycol Coated Liposomes," Cancer Research 54:987–992 (1994).

Thierry et al, "Effect of Liposomes on P–glycoprotein Function in Multi–drug Resistent Cells," Biochem. Biophys. Res. Comm. 187:1098–1105 (1992).

Rahman et al, "Liposome–mediated Modulation of Multidrug Resistance in Human HL–60 Leukemia Cells," J. Natl. Cancer Inst. 84:1909–1914 (1992).

Mayer et al, "Influence of Vesicle Size, Lipid Composition, and Drug–to–Lipid Ratio on the Biological Activity of Liposomal Doxurubicin in Mice," Cancer Research 49:4922–5930 (1989).

Acton et al, "Intensely Potent Morpholinyl Anthracyclines," J. Med. Chem. 27:638–645 (1984).

Priebe et al, "Removal of the Basic Center From Doxurubicin Partially Overcomes Multidrug Resistance and Decreases Cardiotoxicity," Anticancer Drugs 4:37–48 (1993).

Barbieri et al, "Chemical and Biological Characterization of 4'–iodo–4'–deoxydoxorubicin," Cancer Research 47:4001–4006 (1987).

Perez–Soler et al, "Cellular Pharmacology of the Partially Non–Cross–Resistent Anthracycline Annamycin Entrapped in Liposomes in KB and KB–VI Cells," Cancer Research 34:109–118 (1994).

Perez–Soler et al, "Phase I Clinical and Pharmacology Study of Lipsome–Entrapped Cis–bis–neodecanoato–trans–R, R–1,2–diaminocyclohexane–platinum (II)," Cancer Research 50:4254–4259 (1990).

Murray et al, "Phase I Trial of Liposomal Muramyl Tripeptide Phosphati–dylethanolamine in Cancer Patients," J. Clin. Oncol. 7:1915–1925 (1989).

Zou et al, "Organ Distribution and Tumor Uptake of Annamycin, A New Anthracycline Derivative with High Affinity for Lipid Membranes, Entrapped in Multilamellar Vesicles," Cancer Chemother. Pharmacol. 32: 190–196 (1993).

Zou et al, "Quantitative Analysis of the Lipophilic Doxurubicin Analogue Annamycin in Plasma and Tissue Samples by Reverse–Phase Chromatography," J. Pharmaceutical Sci., 82(11):1151–1154 (1993).

Gu et al, "Study on the Polyphase Liposomes — A New Dosage Form for Anti–tumor Drugs. I Antitumor Activity Screening of Polyphase Liposome 139 and Others," Chinese Herb Medicine, 13(4):13–19 (1982).

Zou et al, "Stability and Some Other Important Physical Properties of Polysaccharides Polyphase Liposome (PPL)," Acta Pharmaceutica Sinicia, 24(1):58–62 (1989).

Young et al, "The Anthracycline Antineoplastic Drugs," N. Engl. J. Med., 305(3):139–153 (1981).

Pazdur et al, "Phase I Trial of Taxotere: Five–Day Schedule," J. Natl. Cancer Inst. 84:1781–1788 (1992).

FIG. 1B
ANNAMYCIN

FIG. 1A
DOXORUBICIN

SUBMICRON LIPOSOME SUSPENSIONS OBTAINED FROM PRELIPOSOME LYOPHILIZATES

FIELD OF THE INVENTION

This invention is concerned with an aqueous/t-butanol solvent-system, facile-reconstitute, submicron-reconstitute preliposome-lyophilate. In one embodiment, the preliposomal lyophilate, upon reconstitution into liposomes in the presence of aqueous solution, provides liposomes of submicron size (diameter) distribution. In particular embodiments, size distribution is below about 400 nm, and in a further embodiment, between 400 nm yet above 200 nm, and further including from about 300 nm to about 400 nm diameter liposomes, and in some instances in the 200–150 nm range.

BACKGROUND OF THE INVENTION

A barrier to the successful commercialization of liposomes has been the absence of adequate control over the methods for manufacturing liposomes in large quantities. For regulatory and therapeutic concerns, reproducible products are a necessity. There are numerous published methods for liposome production. Two significant technical concerns govern the commercial usefulness of production methods: content uniformity, and sterility. Hitherto, those production methods that produced liposomes of acceptable content uniformity and sterility had the ancillary problem of size regulation. Previous to the present invention, formulations of preliposome-lyophilate, upon reconstitution, were distributed over a range of diameters larger than 1 micron. This has proven less than ideal for particular therapeutic applications, particularly as to applications benefited from avoidance of the RES.

The use of less than 4% surfactant has been reported (22) to yield stable liposomal preparations. However, the reported procedure required evaporation of toxic organic solvents to prepare a lipid film. Formation of submicron liposomal preparations from such system required sonication. This procedure results in retained organic solvents at levels unsuitable for clinical formulations. Further reconstitution of a thin film presents a material not suitable as a precursor for liposomal preparation due to the substantial difficulty in reconstitution.

Japanese Patent Application No. 91-177731 (Pub. No. 6-183953) (25) discusses a preparation of micelles and what are described as "small vesicles" obtained by treating mixture of phospholipid and nonionic polyoxyethylene surfactant with ultrasonic waves in aqueous solution. The described procedure entails 5% or more of surfactant. No lyophilization of this material was reported.

Japanese Patent Application No. 93-13786 (Pub. No. 6-227966) (26) discusses a thermosensitive liposome preparation for releasing anticancer drug comprising up to 30% nonionic surfactant and phospholipid. This preparation was not disclosed to be lyophilized.

The original liposome preparation of Bangham, et al. (*J. Mol. Biol.*, 1965, 12:238–252) involves dissolving phospholipids in an organic solvent which is then evaporated to dryness leaving a phospholipid film on the reaction vessel. Next, an appropriate amount of aqueous phase is added, the mixture is allowed to "swell," and the resulting liposomes which consist of multilamellar vesicles (MLVs) are dispersed by mechanical means. This technique provides the basis for the development of the small sonicated unilamellar vesicles described by Paphadjopoulos et al. (*Biochim. Biophys. Acta.*, 1968, 135:624–638), and large unilamellar vesicles.

Unilamellar vesicles are produced using an extrusion apparatus by a method described in Cullis et al., PCT Application No. WO 87/00238, published Jan. 16, 1986, entitled "Extrusion Technique for Producing Unilamellar Vesicles" incorporated herein by reference. Vesicles made by this technique, called LUVETS, are extruded under pressure through a membrane filter.

Another class of liposomes are those characterized as having substantially equal lamellar solute distribution. This class of liposomes is denominated as stable plurilamellar vesicles (SPLV) as defined in U.S. Pat. No. 4,522,803 to Lenk, et al., monophasic vesicles as described in U.S. Pat. No. 4,558,579 to Fountain, et al. and frozen and thawed multilamellar vesicles (FATMLV) wherein the vesicles are exposed to at least one freeze and thaw cycle; this procedure is described in Bally et al., PCT Publication No. 87/00043, Jan. 15, 1987, entitled "Multilamellar Liposomes Having Improved Trapping Efficiencies," each of which are incorporated herein by reference. Honda et al. Japanese Patent Pub. No. 60-155109 describes hydrogenated liposomes requiring 5% fatty acid.

Anthracycline antibiotics, namely doxorubicin (Dox), daunorubicin and idarubicin, are among the most effective and widely used anticancer agents. However, their use is limited by acute side effects, mainly acute myelosuppression and chronic cardiotoxicity and natural or acquired drug resistance (1, 2). Liposomes have been extensively studied by different investigators as carriers of this class of compounds. Liposome incorporation has been shown to reduce the cardiotoxicity of Dox in animals (3) and its gastrointestinal side effects and vesicant activity in humans (4). Tumor-targeted formulations of liposomal-Dox are now being evaluated in humans (5). Other interesting studies have shown that multidrug resistance (MDR), a common mechanism of acquired resistance to anthracyclines and other drugs, may be overcome in vitro and in vivo in bone marrow cells by using Dox encapsulated in liposomes containing certain lipids such as cardiolipin or phosphatidylserine (6,7).

The development of pharmaceutical formulations of liposomal-Dox has encountered a great number of technical problems due to the tendency of Dox to leak from the internal aqueous space of the lipid vesicles into the external aqueous milieu. The development of the remote loading technique, which basically consists of keeping the drug protonated inside the liposomes by creating an acidic pH, thus abrogating its ability to cross the liposome membrane, has resulted in formulations with optimal encapsulation efficiencies (8). Still, all liposomal formulations of Dox currently in clinical trials consist of small unilamellar vesicles in suspension and, therefore, particle size stability due to aggregation of particles remains a potential problem.

An alternative approach to enhance the therapeutic index of this class of compounds is the use of new and potentially less toxic and more active analogs. Although a great number of analogs have been synthesized and studied, most of these efforts took place before the phenomenon of MDR was described and well characterized. However, during the last few years, several sub-families of anthracyclines with non cross-resistance properties have been described (9, 10, 11). Because most of them are highly lipophilic and, therefore, not suitable for i.v. administration in water solutions, they require the development of a delivery system for their i.v. administration.

There is a continuing need for improved anticancer drugs, and particularly for improved formulations for delivering anticancer agents to the appropriate sites in a patient's body, while minimizing undesirable side effects.

SUMMARY OF THE INVENTION

The present invention in one aspect, comprises an aqueous/t-butanol solvent-system, facile-reconstitute, submicron-reconstitute preliposome-lyophilate. The preliposome-lyophilate comprises a surfactant, which can be anionic, cationic or nonionic, and is preferably a Tween surfactant, with Tween 20 being most preferred. The surfactant preferably comprises from less than about 4 mole % to about 0.1 mole % of the lipid content of the submicron-reconstitute preliposome-lyophilate, and most preferably about 3 mole % to about 2 mole % of the lipid content of the submicron-reconstitute preliposome-lyophilate. We have found that the use of greater than about 4% and particularly 5% or more surfactant will have a severe adverse effect on liposome integrity. When less than about 4% surfactant is used, the hydration time of the preliposome lyophilizates is reduced to about 1 minute or less, drug crystallization and formation of liposome particle aggregates are prevented or substantially reduced, and the liposome size is reduced to about 400 nm or less, as compared to liposomes containing no surfactant. The "no surfactant" condition results in liposomes in the 1 to 2 micron range. With the present invention, mere hand shaking a vial will result in formation of liposomes of less than about 1 μm. and particularly less than about 400 nm, and particularly in the 200 to 150 nm range.

In another embodiment, the present invention relates to a method of preparing submicron liposomes from lyophilate, comprising introducing surfactant into liquid to be lyophilized prior to said lyophilization. The surfactant can suitably be as described above.

In another aspect, the present invention relates to a method of restricting, to submicron size, liposomes formed by reconstitution of material comprising lipid forming agent, the method comprising introducing a surfactant into said material prior to, or at the time of, reconstitution.

In another embodiment, the present invention concerns a sterically antigenicity-hindered liposome, which comprises a steric-hindering agent, such as, for example, a nonionic surfactant.

In another embodiment, the present invention relates to liposomal formulations of anthracycline compounds. We have extensively explored the use of liposome carriers for the delivery of lipophilic and non cross-resistant anthracyclines. The objectives of our approach were to select compounds with a natural affinity for liposome membranes (therefore, easy to incorporate within the lipid membranes of a wide variety of liposomes) and use liposomes with optimal pharmacological properties (enhanced tumor targeting) as carriers for their i.v. administration (12). As a result of these efforts, Annamycin was selected as the leading compound with these characteristics. We have previously reported that liposomal Annamycin is not cross-resistant with Dox in vitro and in vivo and is less cardiotoxic (13,14).

Lyophilization of preformed liposomes or of the liposome constituents followed on the day of use by reconstitution with an aqueous solution to obtain the liposome suspension has been successfully explored by us and others in the past (15, 16). Potential problems with formulations using preliposomal lyophilized powders are basically related to difficulties encountered with the reconstitution step to obtain a reproducible liposomal suspension. In this patent, we describe a modified lyophilization method for the preparation of a highly stable, easy to reconstitute, submicron liposome suspension of the lipophilic anthracycline Annamycin and we report on the crucial role played by a small amount of the surfactant Tween 20 in improving the characteristics of the formulation.

The present invention in one aspect concerns a pharmaceutical composition, comprising an anthracycline compound having the formula encapsulated in a liposome. One of X and X' is hydrogen and the other is halogen; one of Y and Y' is hydrogen and the other is selected from the group consisting of hydrogen, hydroxy, and —OCOR; and one of Z and Z' is hydrogen and the other is selected from the group consisting of hydrogen, hydroxy, and —OCOR. R is alkyl having approximately 1–6 carbon atoms. The liposome comprises at least one lipid and a nonionic surfactant, and the weight ratio of the anthracycline compound to the nonionic surfactant is between approximately 0.3:1 and approximately 3:1.

"Encapsulate," "entrap," and "incorporate" are used in this patent to mean enclosed within a lipid vesicle or otherwise contained somewhere within the walls of a liposome.

In a preferred embodiment of the invention, the anthracycline compound is Annamycin. The surfactant preferably comprises a polyoxyethylene sorbitan carboxylate, with the carboxylate portion of the surfactant molecule having between approximately 2 and approximately 25 carbon atoms. Examples of suitable carboxylate moieties are monopalmitate, monostearate, tristearate, monooleate, and trioleate. A particularly preferred surfactant comprises a polyoxyethylene sorbitan monolaurate, such as the commercially available surfactant Tween 20. In that embodiment of the invention, the weight ratio of the anthracycline compound to the nonionic surfactant is preferably approximately 1:1.7, the liposome preferably comprises the lipids dimyristoyl phosphatidyl choline and dimyristoyl phosphatidyl glycerol in a molar ratio of approximately 7:3, and the weight ratio of the anthracycline compound to lipid is between approximately 1:40 and approximately 1:100, most preferably about 1:50.

In another aspect, the present invention relates to a preliposome lyophilized powder composition which comprises an anthracycline compound as described above, preferably Annamycin, at least one lipid suitable for forming a liposome when hydrated, and a nonionic surfactant as described above. This powder composition can be reconstituted into an aqueous liposome composition through hydration, as described in more detail below.

In another aspect, the present invention relates to a method of preparing a preliposome lyophilized powder composition, comprising the steps of
  (a) preparing a first solution consisting essentially of an anthracycline compound as described above and dimethyl sulfoxide;
  (b) preparing a second solution comprising at least one lipid, t-butyl alcohol, and water;
  (c) preparing a third solution by combining the first solution and the second solution in the proportions needed to provide the desired ratio of lipid to anthracycline compound in the final composition;

(d) adding to the third solution a nonionic surfactant in an amount that provides a ratio of anthracycline compound to surfactant in the final composition of between approximately 0.3:1 and approximately 3:1;

(e) sterilizing the solution by filtration; and (f) freezing and lyophilizing the solution.

In another aspect, the present invention relates to a method of inhibiting the growth of tumor cells in a mammal. The method comprises administering to a mammal an effective amount of a liposome composition as described above.

The present invention has a number of advantages over prior compositions and methods. One important advantage is the reduced size of the liposomes that result from the present invention. The majority of the liposomes are preferably less than 1 μm in diameter, with the diameter in some embodiments being no greater than 0.2 μm. This small liposome size is an advantage because smaller liposomes are more likely to remain in circulation in vivo for prolonged periods of time, thus increasing the chance that they will reach tumor tissue. Without being bond by any particular theory, it is believed that the 200 nm to 400 nm diameter liposomes and further 200–150 nm diameter liposomes avoid "capture" by the RES.

The compositions of the present invention is useful for treatment of certain human malignancies, such as breast cancer, leukemia, sarcomas, colon cancer, and lung cancer. In particular, such uses are facilitated when a bioactive agent is incorporated into the resulting liposomes. In particular instances, incorporation may be at any point, (i.e., prelyophilization, post lyophilization, post hydration).

DETAILED DESCRIPTION OF SPECIFIC EMBODIMENTS

This invention will be better understood with resort to the following definitions.

"Aqueous/t-butanol solvent-system" in referring to a prelipospmal lyophilate shall mean that preparation has been by "aqueous and t-butanol only" means and that there is substantially no trace of organic solvent other than t-butanol and that t-butanol is present at less than about 0.01% and preferably less than about 0.003% in the preliposomal lyophilate. In particular, aqueous/t-butanol solvent-system includes absence of halogenated solvent. It is to be understood that organic solvent or halogen present as a concomitant of a drug associated with or encapsulated in the preliposomal powder of this invention is not included within this calculation.

"Facile-reconstitute" in referring to a preliposomal lyophilate, shall mean full reconstitution with hand-shaking in about 1 minute, to obtain liposomes of about 400 nm or less, with a particular concentration in the 200 to 400 nm range and/or the 200–150 nm range. A particular characteristic of such powder is its fluffy consistency of unique tertiary structure.

"Submicron-reconstitute," in referring to a preliposomal lyophilate, shall mean liposomes of submicron size (diameter) distribution that are formed upon reconstitution into liposomes in the presence of aqueous solution. In particular embodiments, size distribution is below about 400 nm, and in a further embodiment, below about 300 nm, and further including from about 300 nm to about 200 nm diameter liposomes, and further liposomes of about 200 to about 150 nm diameter.

Size distribution, which refers to median diameter unless otherwise stated, is presented here as determined by QUELS methodology using the Nicomp™ program. In addition, size distribution of particular examples in the 200–150 nm range have been confirmed by freeze fracture electron microscopy.

"Preliposome-lyophilate" shall mean a non-aqueous material that will form liposomes upon addition of aqueous solution. In some embodiments the non-aqueous material is dry (as in non-liquid, non-gel) material. Lyophilate is used expansively to include the dry residue of sublimation of frozen liquids from non-volatile materials, the residue of rotoevaporation and similar procedures, and dry compositions that, upon addition of an aqueous phase (with or without agitation) with result in liposomes. It is particularly to be understood that "preliposome-lyophilate" is not in liposomal form at the time of lyophilization.

"Liposomes" shall mean generally spherical structures comprising lipids, fatty acids, lipid bilayer type structures, unilamellar vesicles and amorphous lipid vesicles. Classically, liposomes are completely closed lipid bilayer membranes containing an entrapped aqueous volume. Liposomes may be unilamellar vesicles (possessing a single bilayer membrane) or multilamellar vesicles (onion-like structures characterized by multiple membrane bilayers, each separated from the next by an aqueous layer). The bilayer is composed of two lipid monolayers having a hydrophobic "tail" region and a hydrophilic "head" region. The structure of the membrane bilayer is such that the hydrophobic (nonpolar) "tails" of the lipid monolayers orient toward the center of the bilayer while the hydrophilic "head" orient towards the aqueous phase.

"Tween™" refers to a commercially available nonionic surfactant (ICI Americas Inc.) consisting of a mixture of different length chains of polyoxyethylene linked to a common sorbitan sugar. These polyoxyethylene sugars are also linked to a fatty acid. In the case of Tween™ 20, the composition is polyoxyethylene sorbitan monolaurate (MW approximately 1300). Tween™ 80, is polyoxyethylene sorbitan monooleate (MW approximately 1350). As Tween™ 20 is shown below, w+x+y+z=20.

Other surfactants include Tween, Span, Pluronic and Brij (Sigma Chemical, St. Louis, Mo.).

"Sterically antigenicity-hindered" shall mean at least 75% of the liposomal surface is occluded. Occluded means that at least 90% of the occluded space prevents particles of less than 0.05 μm from penetrating the occluded space. In practice occlusion prevents a contact dependent biological reaction (such as agglutination) when challenged. In particular embodiments of this invention, aqueous/t-butanol solvent-system, facile reconstitute, submicron-reconstitute preliposome-lyophilate reconstitutes into sterically antigenicity-hindered liposomes.

A "steric-hindering agent" is a moiety present about the exposed lipid layer of a liposome. Such agent is typically intercalated into an exposed lipid bilayer, but may also be applied to an exposed lipid surface by covalent linkages, van der Waals forces or hydrogen bonds. Tween surfactants, particularly Tween 20, are examples of such a moiety. Without being bound by any particular theory, it is believed that the fatty acid chain of Tween 20 intercalates into an exposed lipid bilayer, with the sorbitan and polyoxyethylenes external to the liposome.

"Bioactive agents" is used as a broad term to encompass pharmacoactive agents such as antifungals, antineoplastics, antibiotics, adjuvants, or vaccines; contrast agents such as diazo compounds; biological markers or diagnostic substances such as labeled antigens; and drug targeting carrier agents such as galactose-albumin, and the like. Bioactive agents further may include genetic fragments. Annamycin is a bioactive agent.

Annamycin containing submicron-reconstitute preliposome-lyophilate can be prepared by adding 17 mg of Tween 20 to 500 mg of lipid and 10 mg Annamycin. The lipid component can be, for example, dimyristoyl phosphatidyl choline (DMPC) and dimyristoyl phosphatidyl glycerol (DMPG) at a ratio of 7:3 molar. This ratio calculates to a mole percent of approximately 3%; that is of every 100 molecules, 97 are of lipid, there are 3 of Tween 20.

The compositions and methods of this invention possess (or enable) valuable pharmacological properties. They provide for the increased production of sterile uniform liposomes of smaller diameter in the field of parenteral, and particularly intravenous, administration. This effect can be demonstrated, for example, using the method described herein to provide formulations that will not occlude capillaries of the circulatory system of higher mammals.

Thus, these compositions and methods can be used in antibiotic and antineoplastic therapy, such as encountered in treatment of bacterial infections or cancer. The compositions are particularly useful for preparing reconstitutable formulations for preparation in an hospital pharmacy just prior to administration.

The compositions of this invention are generally administered to animals, including but not limited to mammals, including humans. The pharmacologically active compositions of this invention can be processed in accordance with conventional methods of Galenic pharmacy to produce medicinal agents for administration to patients, e.g. mammals including humans.

The compositions of this invention can be employed in admixture with conventional excipients, i.e., pharmaceutically acceptable organic or inorganic carrier substances suitable for parenteral, enteral (e.g., oral or inhalation) or topical application which do not deleteriously react with the active compositions. Suitable pharmaceutically acceptable carriers include but are not limited to water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like which do not deleteriously react with the active compositions. They can also be combined where desired with other active agents, e.g., vitamins.

For parenteral application, particularly suitable are injectable, sterile, aqueous solutions. Ampoules are convenient unit dosages. For topical application, there are employed as nonsprayable forms, viscous to semi-solid or solid forms comprising a carrier compatible with topical application and having a dynamic viscosity preferably greater than water. Suitable formulations include but are not limited to solutions, suspensions, emulsions, creams, ointments, powders, liniments, salves, etc., which are, if desired, sterilized or mixed with auxiliary agents, e.g., preservatives, stabilizers, wetting agents, buffers or salts for influencing osmotic pressure, etc. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., a freon.

It will be appreciated that the actual preferred amounts of active compositions in a specific case will vary according to the specific compositions being utilized, the particular compositions formulated, the mode of application, and the particular situs and organism being treated. Dosages for a given host can be determined using conventional considerations, e.g., by customary comparison of the differential activities of the subject compositions and of a known agent, e.g., by means of an appropriate, conventional pharmacological protocol.

In general, this invention can be successfully practiced wherein the surfactant does not exceed about 4% (w/w) of the final lyophilate powder, excluding drug weight.

EXAMPLE 1

I. MATERIALS AND METHODS

A. Materials

Dimyristoyl phosphatidylcholine (DMPC) and 1,2-dimyristoyl-sn-glycero-3-[phosphor-rac-(1 glycerol)] (DMPG) were obtained as a dry powder from Nippon Fine Chemicals, Inc., Osaka, Japan.

Figure 1A:
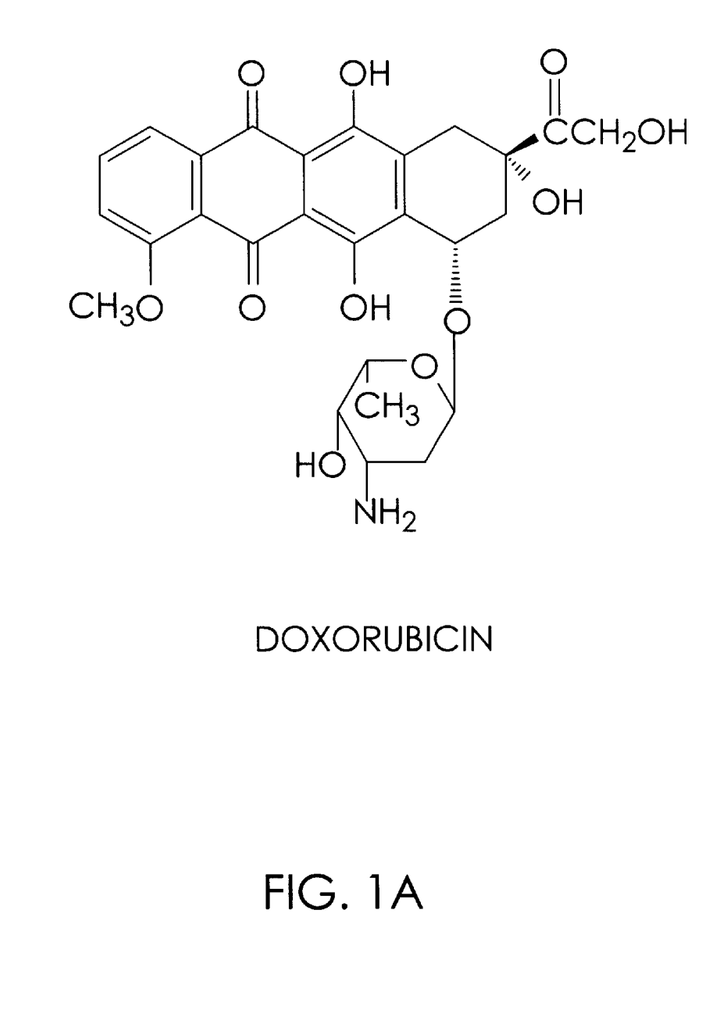
FIG. 1. Chemical structure of (a) doxorubicin and (b) Annamycin.
Figure 1B:
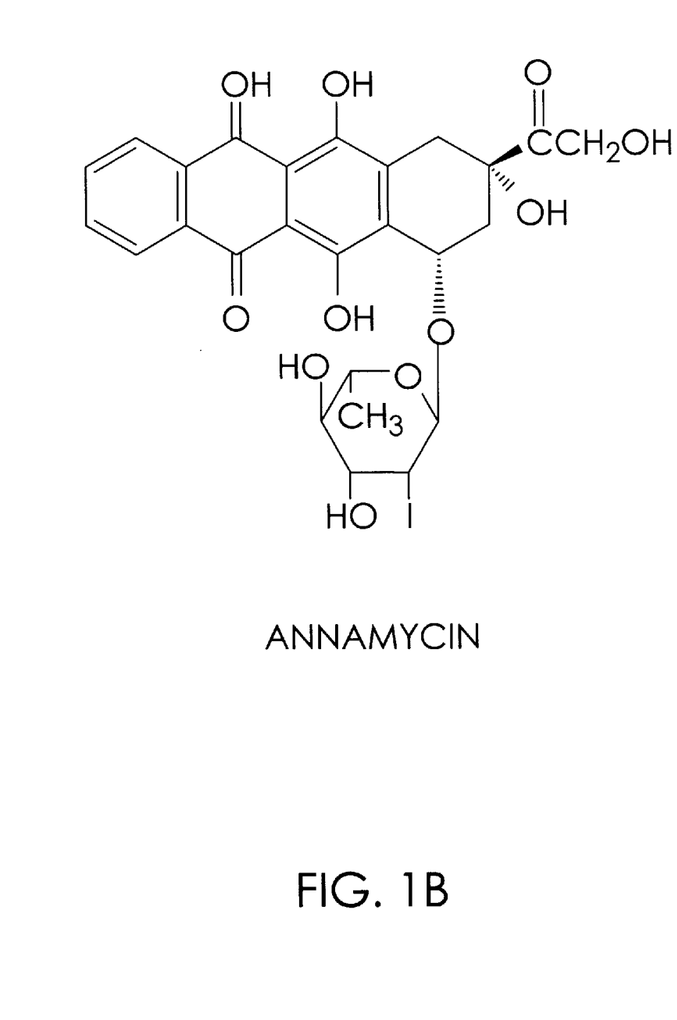

Annamycin (>95% pure) (MW=640.39) (FIG. 1) was synthesized as previously described with slight modifications (17).

Tween 20, DMSO, chloroform and t-butyl alcohol were obtained from Aldrich Chemical Company, Inc., Milwaukee, Wis. Normal saline was obtained from Abbott Laboratories, North Chicago, Ill.

B. Liposome Preparation

The lipid composition was in all cases DMPC:DMPG at a 7:3 molar ratio. Other ratios were also explored but did not result in any significant advantage. Therefore, only results with the 7:3 molar ratio are presented. Different total lipid to drug weight ratios ranging from 10:1 to 100:1 were tested.

The lyophilization method used was adapted from that used by us for other compounds with modifications (15). Briefly, a preliposomal powder is initially prepared by freeze-drying a solution in t-butyl alcohol of the different ingredients and the liposome suspension is obtained by controlled hydration of the preliposomal powder on the day of use. The procedure involves the following general steps:
1. Preparation of preliposomal lyophilized powder.
   a. Solution 1: Annamycin in DMSO (100 mg/ml).
   b. Solution 2: DMPC and DMPG (molar ratio 7:3) in 90% t-butyl alcohol and 10% water (final concentration 81.3 mg lipid/ml).
   c. Solution 3: Solution 1 and 2 in the proportion needed to achieve the desired lipid:drug ratio.
   d. Solution 4: Adding a certain amount of surfactant to Solution 3.
   e. Filtration of solution 4 through a 0.22 $\mu$m pore filter of regenerated cellulose (Micro Filtration Systems) for sterilization.
   f. Aliquots of solution 4 containing 10 mg Annamycin placed in 25 ml lyophilization vials. Vials content frozen over dry ice in acetone.
   g. Lyophilization for 48 hours to remove all DMSO and t-butyl alcohol.
2. Preparation of liposomal Annamycin suspension.
   On the day of use, the preliposomal powder is reconstituted by adding saline prewarmed at 37° C. (1 ml of saline per mg Annamycin) to the lyophilized vial and hand-shaking until all lyophilized material goes into suspension.

C. Liposome Characterization
1. Entrapment efficiency

The entrapment efficiency (% EE) was determined by the differential density centrifugation method previously described (18). Annamycin leakage or dissociation from the liposomes was assessed by sequential determination of the entrapment efficiency over time. % Drug Leakage at x hours=% EE at time 0-% EE at x hours.
2. Size The median liposome size and size distribution were measured in a Nicomp Submicron Particle Sizer (Model 370; Nicomp Particle Sizing System, Santa Barbara, Calif.) by using the Gaussian method.
3. Effect of surfactant The effect of nonionic surfactants (Tween 20 and Tween 80) (polyoxyethylene (20) sorbitan monolaurate and polyoxyethylene (20) sorbitan monooleate, respectively (available from ICI Americas Inc.)) on the liposome size and Annamycin crystallization in the liposome suspension was assessed by fluorescence microscopy at different time points after reconstitution. All preliposome preparations were made using the same procedure but different lipid:drug ratios or surfactant concentrations. The liposome suspension was stored at room temperature (25–26° C.; 60–100 candle foot regular light). Samples from the bottom and middle portions of the reconstituted vials were taken and analyzed at different time points by fluorescence microscopy and sizing. The whole slides were screened twice. The average crystal number/field was obtained from 6 randomly selected fields.
4. Effect of lipid:drug ratio Vials of preliposomal Annamycin preparations using different lipid:drug ratios (with or without surfactant) were reconstituted. Drug crystallization was assessed every 10 min for 1 hour, every hour from 1 to 6 hours, and daily from day 1 to day 7 after reconstitution using fluorescence microscopy as described above.
5. Chemical stability of Annamycin The chemical stability of Annamycin in the lyophilized powder or the liposome suspension was assessed by quantitating the amount of intact Annamycin remaining over time. The quantitation of Annamycin was performed by high performance liquid chromatography using fluorescence detector (excitation wavelength 485 nm, emission wavelength 532 nm) as previously described (19).
6. Physical stability of the liposomes The physical stability of the liposomes was assessed by determining at different time-points after formation of the liposome suspension the % Annamycin leakage, the changes in liposome size distribution and median size, and the de novo appearance of free Annamycin crystals or liposome aggregates as described above.

II. RESULTS

A. Effects of Lipid:drug Ratio and Addition of Surfactant on Liposome Characteristics No problems were encountered in obtaining clear solutions of the lipids and Annamycin in the DMSO, t-butyl alcohol, and water mixture described in Materials and Methods before the addition of surfactant and the freeze-drying step (Solution 3).

The preliposome lyophilized powders obtained were homogeneously flaky and orange in physical appearance. The lipid:drug ratio or the addition of surfactant did not appear to change the physical appearance of the preliposome powders.

Figure 2:
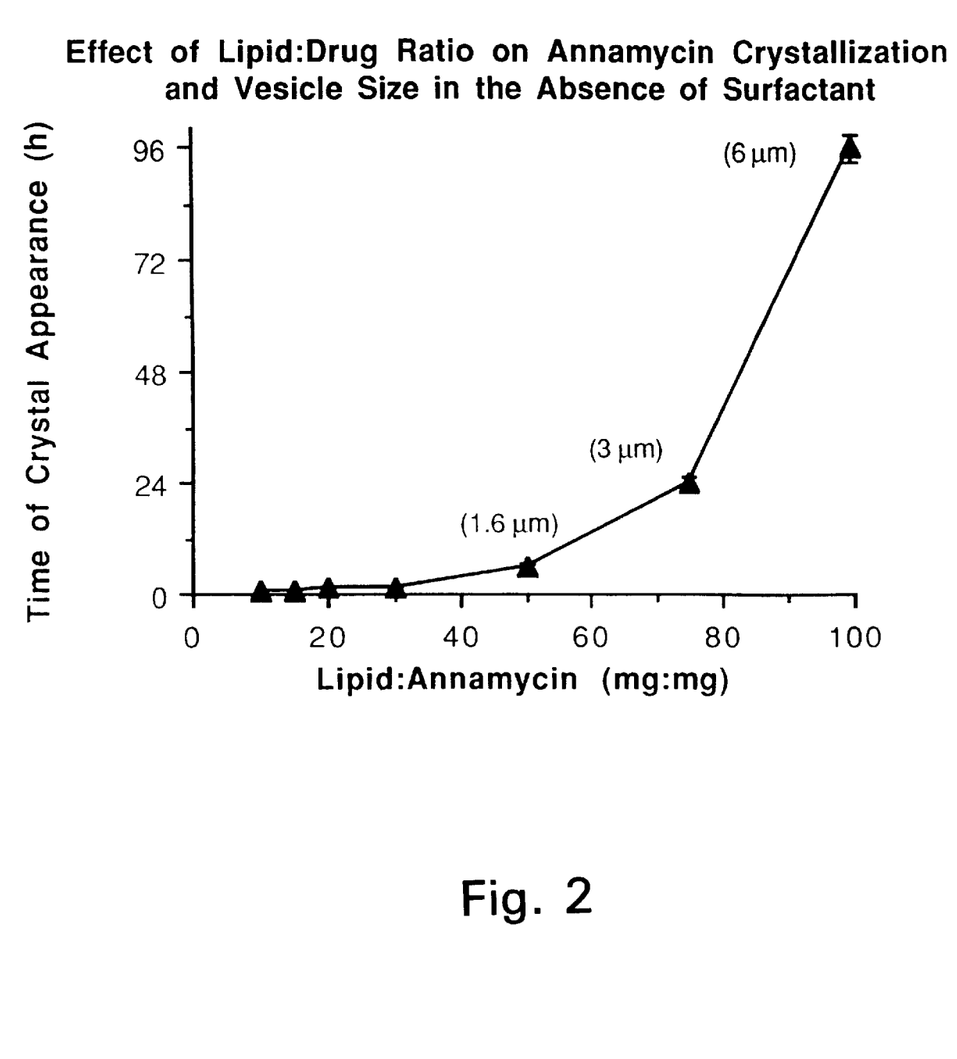
FIG. 2. Effect of lipid:Annamycin weight ratio on the time of appearance of free Annamycin crystals and the median liposome size in the absence of surfactant.

The hydration/reconstitution step and the appearance of the liposome suspensions obtained from preliposome powders using lipid:drug ratios of 10:1 to 25:1 without surfactant presented some obvious problems. Even using saline warmed at 37° C., prolonged hand-shaking (up to 2 hours) was required to obtain a homogeneous suspension without gross aggregates. At the completion of the reconstitution step, typical multilamellar liposome suspensions without the presence of free drug crystals or liposome aggregates were observed on the microscope. However, within a period of minutes, the appearance of free Annamycin crystals was obvious and it became very significant by 6 hours after reconstitution. In an attempt to solve these limitations, we first explored the effect of the lipid:drug ratio on the appearance of free Annamycin crystals and the liposome size. Results are shown in FIG. 2. The appearance of free Annamycin crystals was markedly delayed by increasing the lipid:drug weight ratio to above 25:1. However, the median liposome size was also increased (from about 1.6 $\mu$m at a ratio of 50:1 to about 6 $\mu$m at a ratio of 100:1). Although no crystals were observed in preparations using a lipid:drug weight ratio of 100:1, the amount of lipid required to administer the projected therapeutic doses in humans and the median liposome size were deemed to be excessive and to constitute major shortcomings. As a result, a lipid:drug weight ratio of 50:1 was selected for further formulation optimization studies.

Figure 3:
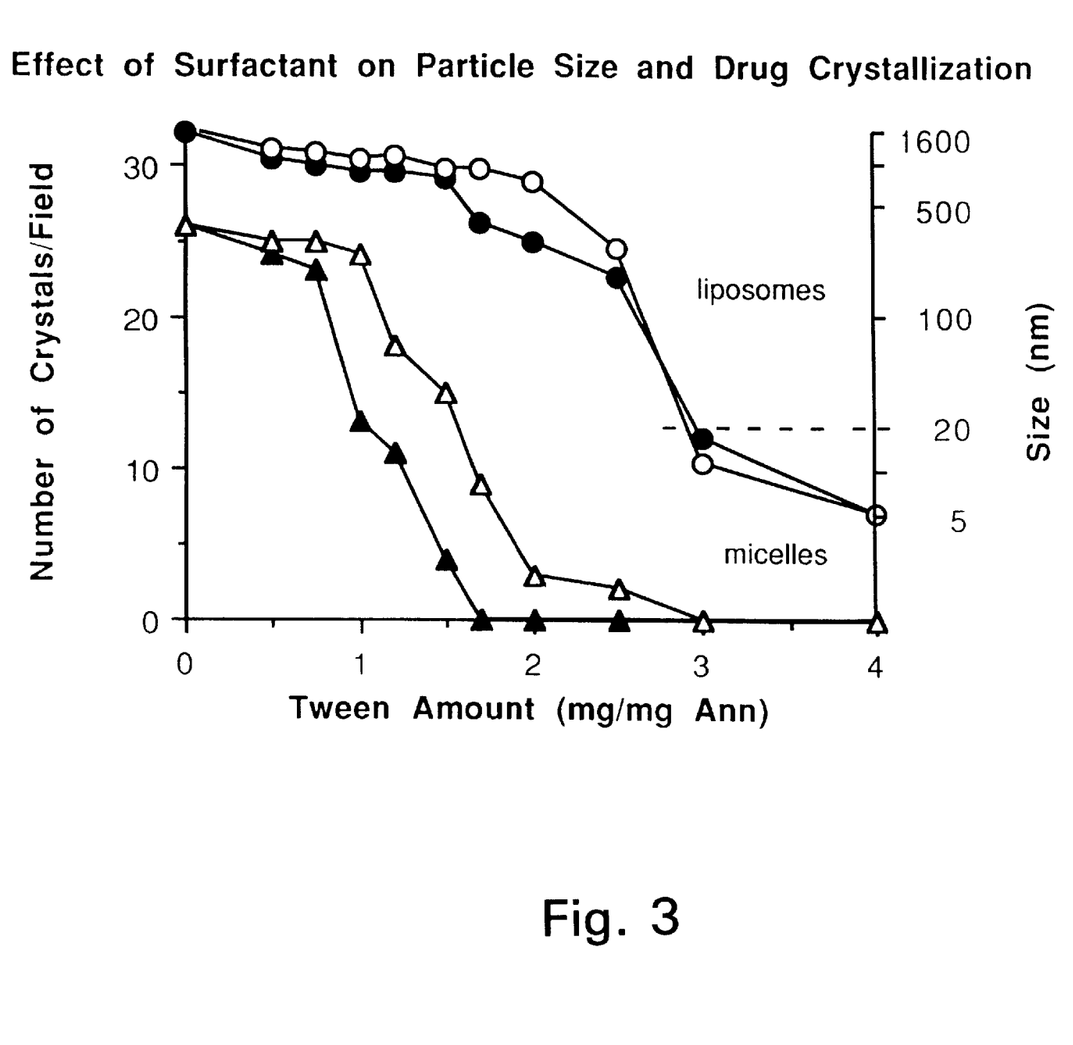
FIG. 3. Effect of the presence of Tween 20 (dark symbols) and Tween 80 (open symbols) on the number of free Annamycin crystals (△, ▲) and the median liposome size (○, ●) 6 hours after reconstitution of the preliposome powder (lipid:Annamycin weight ratio 50:1).

We subsequently studied the effect of the presence of the surfactants Tween 20 and Tween 80 on the liposome size distribution and formation of Annamycin crystals. Amounts of surfactant of 0.5 to 4.0 mg per mg of Annamycin were tested. The lipid:drug ratio was kept constant to 50:1 in these experiments. Results are shown in FIG. 3. Both Tween 20 and Tween 80 completely prevented the formation of free Annamycin crystals at 6 hours after reconstitution in a dose-dependent fashion. No free Annamycin crystals were observed in formulations containing ≧1.7 mg Tween 20 or ≧3.0 mg Tween 80 per mg of Annamycin. Both surfactants reduced also the median liposome size in a dose-dependent fashion. This effect was comparable for both agents and amounts of either surfactant ≧3.0 mg per mg of Annamycin resulted in significant liposome destruction as shown by the appearance of a population of small (<50 nm) particles consistent with micelles. The presence of either surfactant was also found to shorten the time needed to reconstitute the preliposome lyophilized powder. The minimum amount of surfactant completely preventing drug crystallization without liposome disruption was 1.7 mg Tween 20 per mg of Annamycin.

Figure 4:
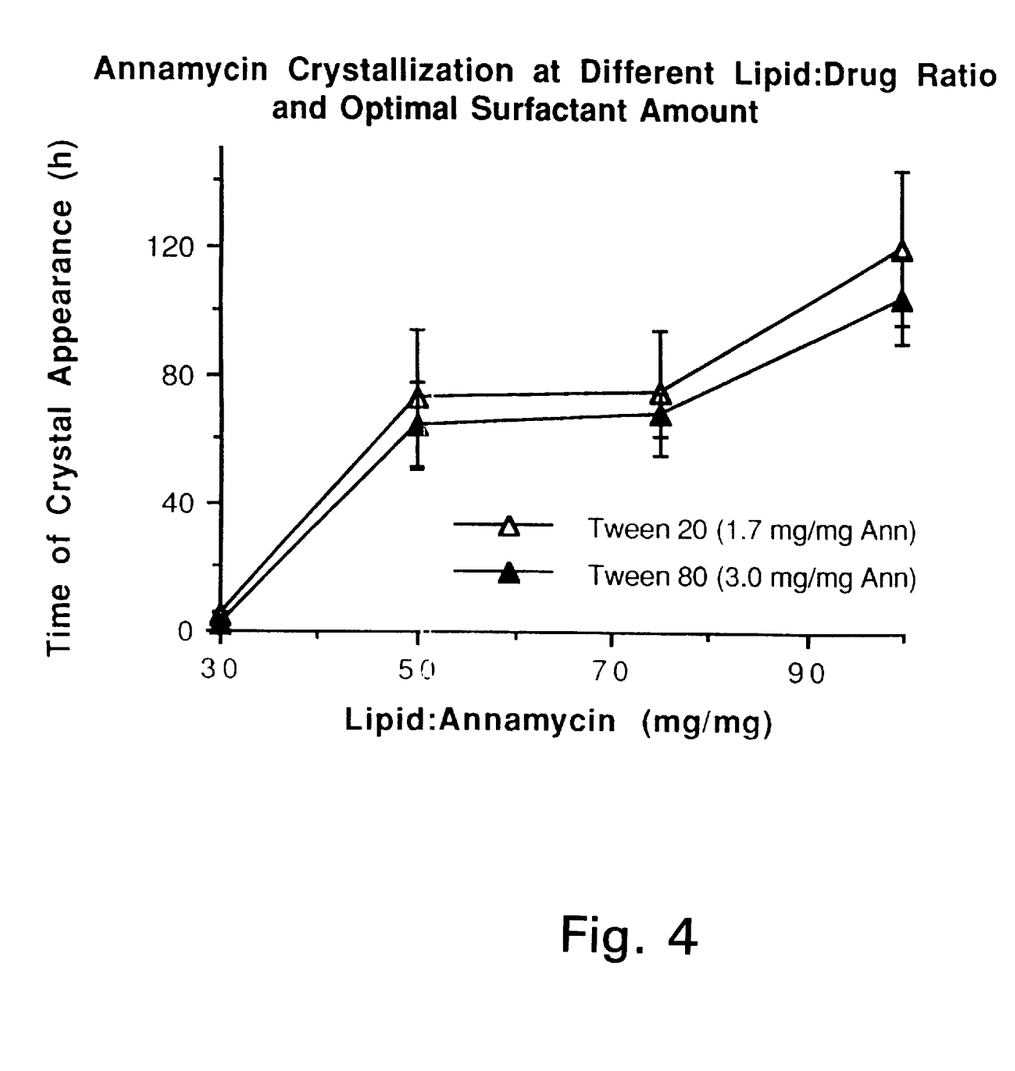
FIG. 4. Effect of lipid:Annamycin weight ratio on the time of appearance of free Annamycin crystals in the presence of optimal amounts of surfactant.

The effect of the lipid:drug ratio on Annamycin crystallization in formulations containing the optimal amount of surfactant was studied next. Results are shown in FIG. 4. The lowest lipid:drug ratio delaying drug crystallization for >48 hours was 50:1. Drug crystallization occurred within a few hours when a lipid:drug ratio of 30:1 was used.

As a result of all these studies, the formulation containing 1.7 mg Tween 20 per mg Annamycin and a lipid:drug ratio of 50:1 was selected for further characterization studies. The characteristics of this formulation are:

1. time of reconstitution of one minute
2. no free Annamycin crystals at 24 hours
3. median size of the liposome suspension: 0.15–0.2 μm
4. no presence of micelles at 24 hours All characterization studies were performed in vials containing 10 mg Annamycin, 500 mg DMPC:DMPG at a 7:3 molar ratio, and 17 mg Tween 20.

B. Characterization of the Selected Liposomal Annamycin Formulation

1. Optic microscopy evaluation

No crystals of free Annamycin or liposome aggregates were observed within 24 hours in all formulations containing Tween 20 (1.7 mg per mg of Annamycin; lipid:drug weight ratio 50:1). Table 1 shows the results obtained with 6 different batches containing Tween 20 and one control batch without Tween 20. Crystals of free Annamycin were clearly observed by fluorescence microscopy as well as sediment seen by direct inspection in the batch not containing Tween 20. None of the Tween 20-containing batches showed crystals or sediment at 24 hours and only one of them showed crystals at 48 hours.

TABLE 1

Characteristics of Six Batches of Liposomal Annamycin

| Parameter | Batch # (Tween 20) | | | | | | Control Batch |
| | 1 | 2 | 3 | 4 | 5 | 6 | No Tween 20 |
| --- | --- | --- | --- | --- | --- | --- | --- |
| % EE | 97.2 | 95.4 | 99.2 | 98.7 | 99.5 | 99.1 | 94.2 |
| Size (nm) | 176 ± 120 | 145 ± 76 | 154 ± 67 | 140 ± 87 | 125 ± 39 | 182 ± 85 | 1558 ± 657 |
| Annamycin Crystals and Sediment | | | | | | | |
| 0 h | — | — | — | — | — | — | — |
| 6 h | — | — | — | — | — | — | c/s |
| 24 h | — | — | — | — | — | — | c/s |
| 48 h | — | — | — | — | — | — | c/s |
| 96 h | s | s | — | — | — | — | c/s |
| 168 h | c/s | s | c/s– | s | — | — | c/s | c = Annamycin crystals seen by optic or fluorescence microscopy;
s = visible sediment;
— = no Annamycin crystals nor sediment.

2. % EE

The % EE in 6 different batches is shown in Table 1. It was >95% in all of them (mean 98.2%).

3. Particle Size

The median particle size and size distribution were determined in the same 6 batches and found to be very reproducible: 182, 154, 176, 140, 145, and 154 nm.

Figure 5:
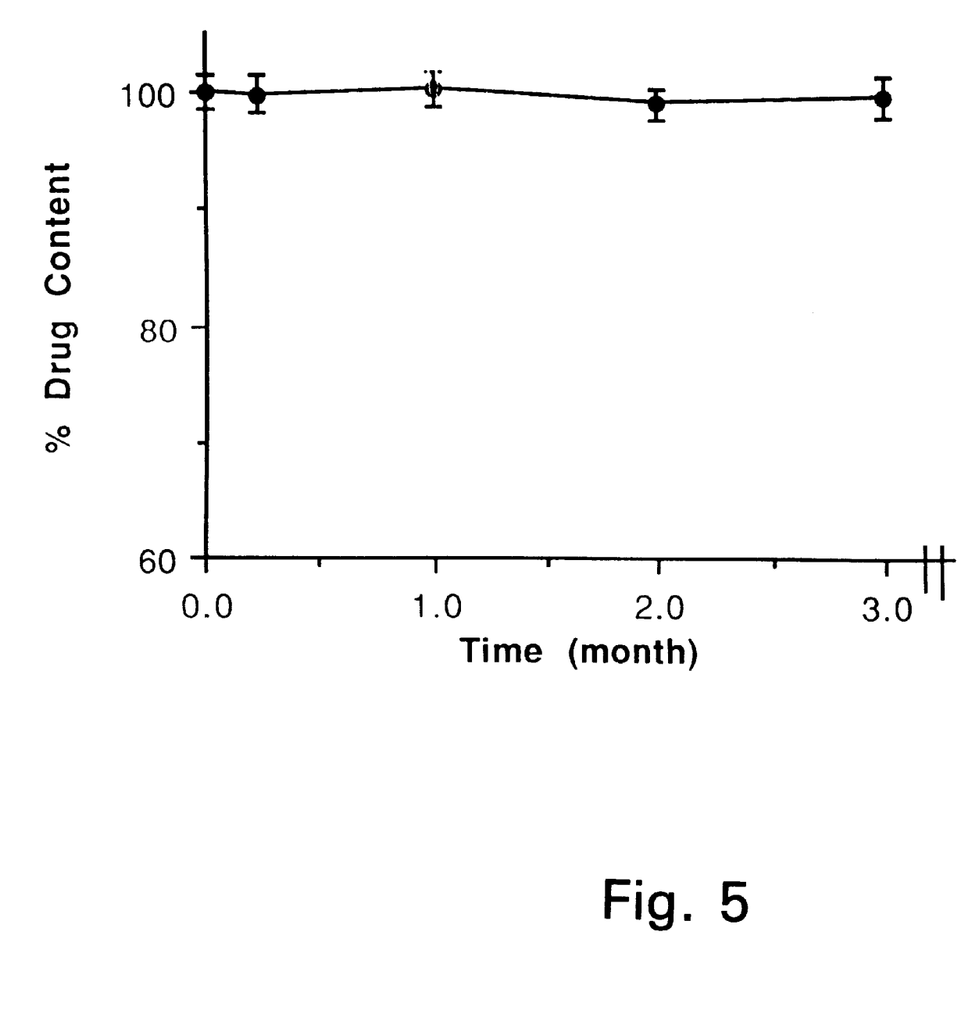
FIG. 5. Chemical stability of Annamycin in the preliposome lyophilized powder stored at room temperature (26±1° C.) and regular light (60–100 foot candle light).

4. Stability Studies a. Chemical stability of Annamycin in the preliposome lyophilized powder FIG. 5 shows the changes in Annamycin content over time (0 to 8 weeks) in 4 different batches of lyophilized Annamycin kept at room temperature and exposed to 60–100 candle foot light. No significant reduction in Annamycin content was detected during this time frame in any of the batches tested.

b. Chemical stability of Annamycin in the liposome suspension

Figure 6:
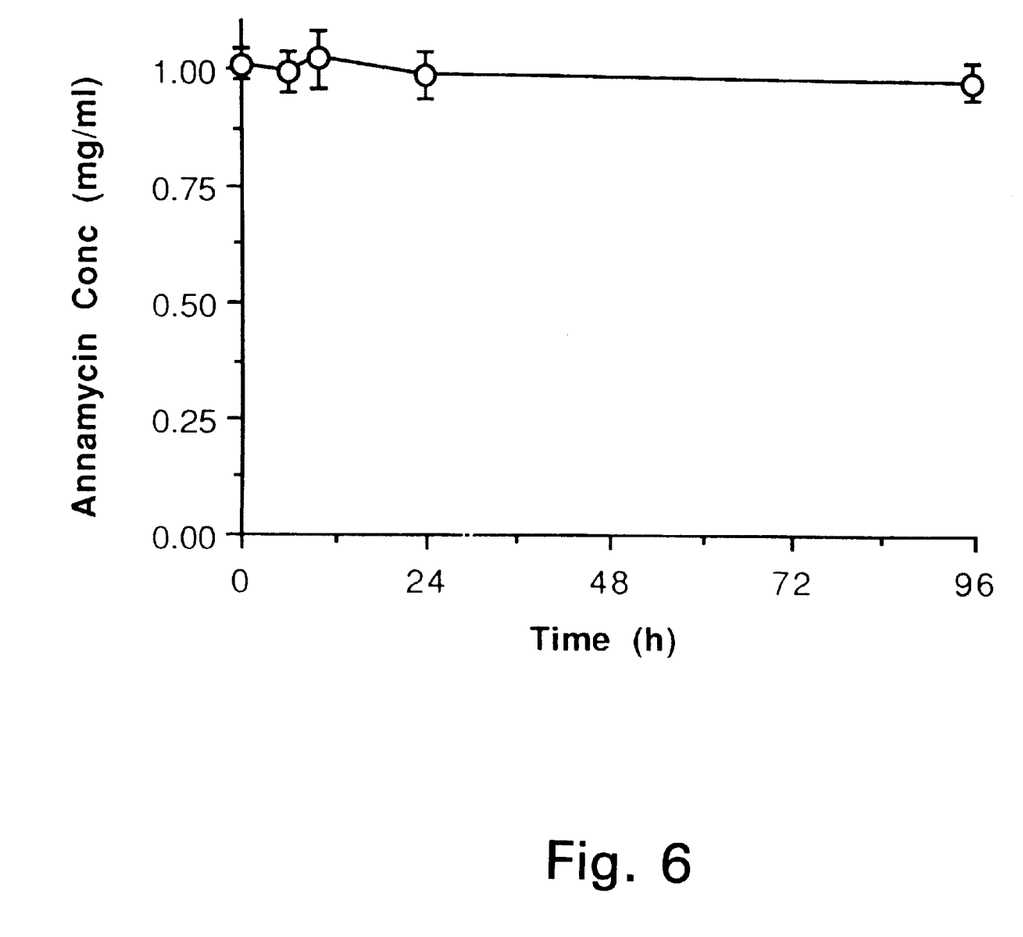
FIG. 6. Chemical stability of Annamycin in the liposome Annamycin suspension stored at room temperature (26±1° C.) and regular light (60–100 foot candle light).

FIG. 6 shows the changes in Annamycin content over time (0 to 168 hours) in 6 different batches of liposomal Annamycin (3 samples per batch) kept at room temperature and exposed to 60–100 candle foot light. No significant reduction in Annamycin content was detected during this time frame in any of the batches tested.

C. Physical stability of liposomal Annamycin:drug leakage and changes in size distribution.

Table 2 shows the changes in % EE and median size of three different batches of liposomal Annamycin kept at room temperature and 60–100 candle foot light. Drug leakage ranged between 0.6 to 1.8% during this period of time and the change in median size between 0.00 and 0.03 μm.

TABLE 2

Physical Stability of Three Batches of Liposomal Annamycin

| Batch No. | Storage hours | % EE | Size (nm) |
| --- | --- | --- | --- |
| 1 | 0 | 97.2 ± 1.3 | 140 ± 87 |
|   | 24 | 95.4 ± 1.4 | 139 ± 68 |
| 2 | 0 | 98.5 ± 1.5 | 167 ± 73 |
|   | 24 | 97.7 ± 1.2 | 168 ± 62 |

TABLE 2-continued

Physical Stability of Three Batches of Liposomal Annamycin

| Batch No. | Storage hours | % EE | Size (nm) |
|---|---|---|---|
| 3 | 0 | 95.6 ± 0.8 | 142 ± 38 |
|   | 24 | 95.0 ± 1.2 | 141 ± 31 |

Reconstitution: warm normal saline (30° C.), 10 ml/vial, 1 min hand-shaking.
Storage conditions: room temperature (26 ± 1° C.), light 60–100 c.f.

III. DISCUSSION

The preceding description shows the effect of small amounts of the surfactant Tween 20 in markedly improving the characteristics of the liposome formulation of the lipophilic anthracycline antibiotic Annamycin. Annamycin was selected among more than 30 lipophilic anthracyclines because of its lack of cross-resistance properties, promising biological activity in different animal models, and easiness of formulation in liposomes as a result of its high affinity for lipid membranes (12,14). However, when the development of a lyophilized liposomal-Annamycin formulation amenable to large scale manufacturing was attempted, problems both in terms of length of the reconstitution step as well as early appearance of Annamycin crystals in the liposome suspension were encountered. The addition of a precise amount of Tween 20 and the use of a specific lipid:drug weight ratio resulted in a complete resolution of these limitations. Furthermore, the presence of Tween 20 decreased by 6–9 fold the median size of the liposomes obtained. This is an advantage since smaller liposomes are not taken as avidly by the reticulo-endothelial system and are, therefore, more likely to remain for prolonged periods of time in circulation, thus increasing their chance of crossing the endothelial barrier and reaching the tumor tissue.

The findings reported here are new and potentially important since they could be applied to the development of liposome formulations of other lipophilic compounds. The amount and type of surfactant needed may, however, vary for each different drug. In the case of Annamycin, the amount and type of surfactant appear to be crucial since higher amounts of Tween 20 were found to disrupt the liposomes and lower amounts did not avoid completely drug crystallization, and in the case of the other surfactant tested, Tween 80, the amounts needed to completely prevent drug crystallization were found to cause significant liposome disruption.

The addition of Tween 80 has been previously reported to enhance the stability and entrapment efficiency of liposomes (20–22) but not to decrease the median size nor reduce the hydration time nor the crystallization of water-insoluble drugs entrapped in liposomes. The mechanisms by which the presence of optimal amounts of surfactant can enhance the hydration step, decrease free drug crystal formation, and reduce the size of the liposomes are unknown and open to speculation. The hydrocarbon tail of Tween 20 may be able to penetrate within the lipid bilayer, thus leaving the polyethylene oxide groups on the surface of the liposomes, which may decrease liposome fusion and the consequent lipid and Annamycin exchange upon collision of liposome particles, as previously suggested (22). This would prevent the association of Annamycin molecules and, consequently, the formation of free drug crystals. Alternatively, Tween 20 may just prevent the free association of Annamycin molecules when the aqueous solution is added to the lyophilized preliposome powder to form the liposomes, thus decreasing the chance of free drug crystal formation. The first mechanism appears more likely since no crystals were observed immediately after reconstitution in the absence of Tween 20, thus indicating that drug crystallization occurs after initial liposome formation.

The liposomal Annamycin preparation described in this patent was used in clinical trial. Its cytotoxicity was tested in vitro against KB cells and compared with the preparation obtained using the evaporation method that we have previously reported (13). The cytotoxicity of both preparations was found to be equivalent. Subacute mouse toxicity studies have also been performed and show that the liposomal preparation obtained by the evaporation method is about twice as toxic as the one obtained from the preliposomal powder containing Tween 20 ($LD_{50}$ 8 mg/kg vs. 16 mg/kg). This difference is probably due to the different size distribution of both preparations.

The presence of Tween 20 can induce allergic reactions in patients. Tween 80 is currently an ingredient in different parenteral formulations approved for clinical use in the U.S. (etoposide, multivitamins, etc.). Tween 80 is also an ingredient of the current formulation of the new antitumor agent Taxotere (23) which is currently under intensive investigation with very promising results. The amount of Tween 80 needed to deliver a therapeutic dose of Taxotere has been calculated to be about 30–50 times higher than the amount of Tween 20 that will be administered with the projected therapeutic dose of liposomal Annamycin. Still, allergic reactions secondary to the presence of Tween 20 are a potential side effect of liposomal Annamycin and premedication to avoid them may be needed in the upcoming clinical trials.

IV. REFERENCES

The following documents are incorporated here by reference.

1. Young, R. C, Ozols, R. F. and Myers, C. E. The anthracycline antineoplastic drugs. N. Engl. J. Med., 305(3), 139–153, 1981.

2. Singer, J. W., Narahara, K. A., Ritchie, J. L., Hamilton, G. W. and Kennedy, J. W. Time- and dose-dependent changes in ejection fraction determined by radionucleotide angiography after anthracycline therapy. Cancer Treatm. Rep., 62(6), 945–948, 1978.

3. Herman, E. H., Rahman, A., Ferrans, V. J., Vick, J. A., Schein, P. S. Prevention of chronic doxorubicin cardiotoxicity in beagles by liposomal encapsulation. Cancer Res. 43, 5427–5432, 1983.

4. Rahman, A., Treat, J., Roh, J. K., Potkul, L. A., Alvord, W. G., Forst, D., Woolley, P. V. A phase I clinical trial and pharmacokinetic evaluation of liposome-encapsulated doxorubicin. J Clin Oncol 8:1093–1100, 1990.

5. Gabizon, A., Catane, R., Uziely, B., Kaufman, B., Safra, T., Cohen, R., Martin, F., Huang, A., and Barenholz, Y. Prolonged circulation time and enhanced accumulation in malignant exudates of doxorubicin encapsulated in polyethylene-glycol coated liposomes. Cancer Res. 54, 987–992, 1994.

6. Thierry, A. R., Dritschilo, A., Rahman, A. Effect of liposomes on P-glycoprotein function in multidrug resistant cells. Biochem Biophys Res Comm 187:1098–1105, 1992.

7. Rahman, A., Husain, S. R., Siddiqui, J., Verma, M., Agresti, M., Center, M., Safa, A. R., Glazer, R. I. Liposome-mediated modulation of multidrug resistance in human HL-60 leukemia cells. J Natl Cancer Inst 84:1909–1914, 1992.

8. Mayer, L. D., Tai, L. C., Ko, D. S., Masin, D., Ginsberg, R. S., Cullis, P. R., Bally, M. B. Influence of vesicle size, lipid composition, and drug-to-lipid ratio on the biological activity of liposomal doxorubicin in mice. Cancer Res 49:5922–5930, 1989.

9. Acton, E. M., Tong, G. L., Mosher, C. W., Wolgemuth, R. L. Intensely potent morpholinyl anthracyclines. J Med Chem 27:638–645, 1984.

10. Priebe, W., Van, N. T., Burke, T. G., Perez-Soler, R. Removal of the basic center from doxorubicin partially overcomes multidrug resistance and decreases cardiotoxicity. Anticancer Drugs 4:37–48, 1993.

11. Barbieri, B., Giuliani, F. C., Bordoni, T., Casazza, A. M., Geroni, C., Bellini, O., Suarato, A., Gioia, B., Penco, S., Arcamone, F. Chemical and biological characterization of 4'-iodo-4'-deoxydoxorubicin. Cancer Res 47:4001–4006, 1987.

12. Perez-Soler, R., Priebe, W. Anthracycline antibiotics with high liposome entrapment structural features and biological activity. Cancer Res. 50:4260–4266, 1990.

13. Perez-Soler, R., Ling, Y-H., Zou, Y., and Priebe, W. Cellular pharmacology of the partially non-cross-resistant anthracycline annamycin entrapped in liposomes in KB and KB-VI cells, Cancer Chemother Pharmacol. 34, 109–118, 1994.

14. Zou, Y., Ling, Y-H., Van, N. T., Priebe, W., and Perez-Soler, R. Antitumor activity of free and liposome-entrapped annamycin, a lipophilic anthracycline with non-cross-resistance properties. Cancer Res. 54, 1479–1484, 1994.

15. Perez-Soler R., Lopez-Berestein, G., Lautersztain, J., Al-Baker, S., Francis. K., Macias-Kiger, D., Raber, M. N., Khokhar, A. R. Phase I clinical and pharmacology study of liposome-entrapped cis-bis-neodecanoato-trans-R,R-1,2-diaminocyclohexane-platinum (II). Cancer Res 50:4254–4259, 1990.

16. Murray, J. L., Kleinerman, E. S., Cunningham, J. E., et al.: Phase I trial of liposomal muramyl-tripeptide-phosphatidyl-ethanolamine [MTP-PE(CGP 19835A)] in cancer patients. J Clin. Oncol. 7:1915–1925, 1989.

17. Horton, D., Priebe, W. 4-demethoxy-3'-desamino-2'-halo-anthracyclines and pharmaceutical compositions containing same. U.S. Pat. No. 4,537,882, 1985.

18. Zou, Y., Priebe, W., Ling, Y., Perez-Soler, R. Organ distribution and tumor uptake of annamycin, a new anthracycline derivative with high affinity for lipid membranes, entrapped in multilamellar vesicles. Cancer Chemother. Pharmacol. 32:190–196, 1993.

19. Zou, Y., Hayman, A., Priebe, W., Perez-Soler, R. Quantitative analysis of the lipophilic doxorubicin analogue Annamycin in plasma and tissue samples by reverse-phase chromatography. J. Pharmaceutical. Sci. 82(11), 1151–1154, 1993.

20. Gu, X-Q., Ma, Z., Li, H-Q., Sun, S., Yao, C., Xin, S., Pei, S., Ma, D., and Tao, J. Study on the polyphase liposomes—a new dosage form for antitumor drugs. I Antitumor activity screening of polyphase liposome 139 and others. Chinese Herb Medicine, 13(4),13–19, 1982.

21. Zou, Y., Su, D-S., Han, G-C., and Gu, X-Q. Stability and some other important physical properties of polysaccharides polyphase liposome (PPL). Acta Pharmaceutica Sinica. 24(1), 58–62, 1989.

22. Kronberg, B., Dahlman, A., Carlfors, J., Karlsson, J., Artursson, P. Preparation and evaluation of sterically stabilized liposomes: colloidal stability, serum stability, macrophage uptake, and toxicity. J. Pharm. Sci, 79(8), 667–671, 1990.

23. Pazdur, R., Newman, R. A., Newman, B. M., Fuentes, A., Benvenuto, J., Bready, B., Moore, D., Jaiyesimi, I., Vreeland, F., Bayssas, M., Raber, M. N. Phase I trial of Taxotere: five-day schedule. J Natl Cancer Inst 84:1781–1788, 1992.

24. Perez-Soler, R., Priebe, W., Lopez-Berestein, G. Liposome compositions of anthracycline derivatives. U.S. Pat. No. 4,863,739, 1989.

25. Japanese Patent Application No. 91-177731 (Pub. No. 6-183953) "Mixed lipid film vesicle having uniform grain size is obtained by treating mixture of phospholipid and nonionic polyoxyethylene surfactant with ultrasonic waves in aqueous solution."

26. Japanese Patent Application No. 93-13786 (Pub. No. 6-227966) "Temperature sensitive liposome preparation releasing anticancer drug comprising nonionic surfactant and phospholipid."

Liposomes in accordance with the present invention can be prepared from various amphipathic substances including natural or synthetic phospholipids. Numerous suitable phospholipids are well known in the art. The liposomes of the present invention can be multilamellar, unilamellar, or have an undefined lamellar construction. A pharmaceutical composition comprising such liposomes can include a pharmaceutically acceptable carrier or diluent. In addition to the surfactants described above, other polyoxyethylene sorbitan carboxylate surfactants which might be used are available from ICI Americas Inc.

Liposome compositions of the present invention can be used in methods of inhibiting the growth of tumor cells in mammals, particularly in humans. The methods involve administering to a mammal an effective amount of the compositions. The administering step can suitably be parenteral and by intravenous, intraarterial, intramuscular, intralymphatic, intraperitoneal, subcutaneous, intrapleural, or intrathecal injection, or by topical application or oral dosage. Such administration is preferably repeated on a timed schedule until tumor regression or disappearance has been achieved, and may be used in conjunction with other forms of tumor therapy such as surgery or chemotherapy with different agents. The dose administered of a composition in accordance with the present invention is preferably between approximately 40 and 100 mg/m$^2$ with respect to the mammalian subject to which it is administered.

The preceding description of specific embodiments of the present invention is not intended to be a complete list of every possible embodiment of the invention. Persons skilled in this field will recognize that modifications can be made to the specific embodiments described here that would be within the scope of the present invention.

We claim:

1. A pharmaceutical composition, comprising annamycin encapsulated in a liposome, where the liposome comprises at least one lipid and a nonionic surfactant, wherein the non-ionic surfactant comprises a polyoxyethylene sorbitan monolaurate, and where the weight ratio of annamycin to surfactant is between approximately 0.3:1 and about 3:1.

2. The composition of claim 1, where the weight ratio of the annamycin to surfactant is approximately 1:1.7.

* * * * *

UNITED STATES PATENT AND TRADEMARK OFFICE
CERTIFICATE OF CORRECTION

| | |
|---|---|
| PATENT NO. | : 5,902,604 |
| APPLICATION NO. | : 08/468791 |
| DATED | : May 11, 1999 |
| INVENTOR(S) | : Yiyu Zou et al. |

It is certified that error appears in the above-identified patent and that said Letters Patent is hereby corrected as shown below:

In Column 1, line 4, please insert --This invention was made with government support under CA050270 awarded by The National Institutes of Health. The government has certain rights in the invention.--.

Signed and Sealed this

Fifteenth Day of April, 2008

JON W. DUDAS
*Director of the United States Patent and Trademark Office*